United States Patent [19]

Knifton

[11] Patent Number: 4,605,677
[45] Date of Patent: Aug. 12, 1986

[54] PROCESS FOR $C_1$–$C_4$ ALKANOL PRODUCTION FROM SYNTHESIS GAS

[75] Inventor: John F. Knifton, Austin, Tex.

[73] Assignee: Texaco Inc., White Plains, N.Y.

[21] Appl. No.: 780,348

[22] Filed: Sep. 26, 1985

[51] Int. Cl.$^4$ .............................................. C07C 27/06
[52] U.S. Cl. .................................... 518/700; 502/164
[58] Field of Search ........................................ 518/700

[56] References Cited
U.S. PATENT DOCUMENTS
4,332,915 6/1982 Knifton et al. ...................... 518/700

FOREIGN PATENT DOCUMENTS
0098031 1/1984 European Pat. Off. ............ 518/700

Primary Examiner—Howard T. Mars
Attorney, Agent, or Firm—Jack H. Park; Kenneth R. Priem; Cynthia L. Kendrick

[57] ABSTRACT

This invention concerns a process for making $C_1$–$C_4$ alkanols and particularly ethanol which comprises contacting a mixture of CO and $H_2$ at a pressure of 30 atm or greater and at a temperature of at least 150° C. with a catalyst system comprising a ruthenium-containing compound and a cobalt-containing compound dispersed in a low melting quaternary phosphonium base with an added N-heterocyclic promoter.

17 Claims, No Drawings

4,605,677

PROCESS FOR C$_1$–C$_4$ ALKANOL PRODUCTION FROM SYNTHESIS GAS

BACKGROUND OF THE INVENTION

1. Field of the Invention

This invention concerns an improved process for C$_1$–C$_4$ alkanol production from synthesis gas under moderate pressure. An improvement in the selectivity of alcohol relative to ester is achieved with promoters, with C$_1$–C$_4$ alkanols making up to 66 wt % of the total liquid product. In addition to improved selectivity for C$_1$–C$_4$ alkanols, there is improved selectivity for ethanol which comprises up to 54% of that fraction.

2. Prior Art

It has long been known that monofunctional alcohols such as methanol, ethanol, etc. can be formed by the reaction of synthesis gas, i.e., a mixture of carbon monoxide and hydrogen at elevated pressures of, for example, up to 1000 atmospheres, and at temperatures of from about 200° to 500° C. or more using as a catalyst a mixture of copper, chromium and zinc oxides. A wide variety of other catalysts have been employed in the reaction of carbon monoxide and hydrogen to yield liquid products containing substantial amounts of monofunctional alcohols as exemplified by methanol, ethanol, propanol, etc. For example, in U.S. Pat. No. 4,013,700 the reaction of carbon monoxide and hydrogen in the presence of a quaternary phosphonium cation and a rhodium carbonyl complex yields a liquid product having a high methanol content. In U.S. Pat. No. 4,014,913 where the same reactants are contacted with a solid catalyst comprising a combination of rhodium and manganese the product formed contains substantial amounts of ethanol and in U.S. Pat. No. 4,197,253 where the reaction of carbon monoxide and hydrogen is conducted in the presence of a rhodium carbonyl complex and a phosphine oxide compound the resulting product contains a high concentration of methanol. Likewise, when the same reactants are contacted with a rhodium carbonyl complex and a copper salt a liquid product containing a substantial amount of methanol is formed.

One serious problem associated with synthesis gas operations in the past has been the non-selectivity of the product distribution since high activity catalysts generally yield a liquid product containing numerous hydrocarbon materials. Thus, complicated recovery schemes are necessary to separate the desired product and the overall yield of the valuable organic products is low. This is a definite need in the art for a process which will produce alkanols, especially ethanol-rich alkanols, with a high degree of selectivity from synthesis gas.

The discovery of a process for making alkanols at moderate pressures, with improved selectivity for ethanol by using a unique catalyst system with a novel promoter would be an advance in the art. The ethanol, methanol, propanol and butanol would be useful as octane enhancers for gasoline blending.

SUMMARY OF THE INVENTION

This invention concerns a method for making C$_1$–C$_4$ alkanols, especially ethanol, which comprises contacting a mixture of CO and H$_2$ at a pressure of 30 atm or greater and at a temperature of at least 150° C. with a catalyst system comprising a ruthenium-containing compound and a cobalt-containing compound dispersed in a low melting quaternary phosphonium salt with added N-heterocyclic promoters.

DETAILED DESCRIPTION OF THE INVENTION

In the narrower and more preferred practice of this invention, C$_1$–C$_4$ alkanols, especially ethanol, are prepared by contacting a mixture of CO and H$_2$ at a temperature of about 150° to about 350° C. and at a pressure of 30 atm or greater with a catalyst system comprising one or more ruthenium-containing compounds and one or more cobalt-containing compounds dispersed in a low melting quaternary phosphonium salt with added N-heterocyclic promoters such as 2,2'-dipyridyl.

As previously pointed out the catalyst system employed in the practice of this invention contains one or more ruthenium-containing compounds and one or more cobalt-containing compounds. The ruthenium-containing catalyst as well as the cobalt-containing catalyst may be chosen from a wide variety of organic or inorganic compounds, complexes, etc., as will be shown and illustrated below. It is only necessary that the catalyst precursor actually employed contain the metals in any of their ionic states. The actual catalytically active species is then believed to comprise ruthenium and cobalt in complex combination with the quaternary salt, promoter and with carbon monoxide and hydrogen. The most effective catalysis is believed to be achieved where ruthenium and cobalt hydrocarbonyl species are solubilized in a quaternary phosphonium salt with an N-heterocyclic promoter under reaction conditions.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as H$_2$Ru$_4$(CO)$_{13}$ and H$_4$Ru$_4$(CO)$_{12}$, and substituted carbonyl species such as the tricarbonylruthenium(II) chloride dimer, [Ru(CO)$_3$Cl$_2$]$_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The cobalt-containing catalyst precursors may take many different forms. For instance, the cobalt may be added to the reaction mixture in an oxide form, as in the case of, for example, cobalt(II) oxide (CoO) or cobalt(II,III) oxide (Co$_3$O$_4$). Alternatively, it may be added as the salt of a mineral acid, as in the case of cobalt(II) nitrate, hydrate (Co(NO$_3$)$_2$.6H$_2$O), cobalt(II) sulphate, etc., or as the salt of a suitable organic carboxylic acid, for example, cobalt(II) formate, cobalt(II) acetate, cobalt(II) propionate, cobalt(II) oxalate, cobalt naphthenate, as well as cobalt complexes with carbonyl-containing ligands as in the case of cobalt(II) acetylacetonate and cobalt(III) acetylacetonates, etc. The cobalt may also be added to the reaction zone as cobalt carbide, cobalt(II) carbonate and a carbonyl or hydrocarbonyl derivative. Here, suitable examples include dicobalt octacarbonyl ($Co_2(CO)_8$), cobalt hydrocarbonyl ($HCo(CO)_4$) and substituted carbonyl species such as the triphenylphosphine cobalt tricarbonyl dimer, etc.

Preferred cobalt-containing compounds include oxides of cobalt, cobalt salts of organic carboxylic acids and cobalt carbonyl or hydrocarbonyl derivatives. Among these, particularly preferred are cobalt(II) acetylacetonate, cobalt(III) acetylacetonate, cobalt(II) acetate, cobalt(II) propionate, and dicobalt octacarbonyl.

The ruthenium-containing compound and cobalt-containing compound are, prior to their catalytic use in making alkanols, first dispersed in a low melting quaternary phosphonium salt. It is interesting to note that the ruthenium-containing compound alone, without being dispersed in said salt, has little, if any activity in promoting the manufacture of alkanols from synthesis gas.

The quaternary phosphonium salt must be relatively low melting, that is, melt at a temperature less than about the temperature of reaction of making alkanols. Usually the quaternary compound has a melting point less than about 180° C., and most often has a melting point less than 150° C.

Suitable quaternary phosphonium salts have the formula:

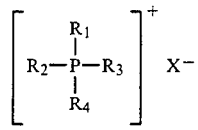

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$–$C_{10}$ alkyl substituents, bonded to the phosphorus atom through the aryl function.

Illustrative examples of suitable quaternary phosphonium salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium chromate, tetrabutylphosphonium tetrafluoroborate and tetrabutylphosphonium acetate. Table I provides evidence of the effectiveness of the quaternary phosphonium salts when in combination with triruthenium dodecacarbonyl.

The preferred quaternary salts are generally the tetralkylphosphonium salts containing alkyl groups having 1-6 carbon atoms, such as methyl, ethyl and butyl. Tetrabutylphosphonium salts, such as tetrabutylphosphonium bromide, are most preferred for the practice of this invention.

Preferred tetrabutylphosphonium salts include the bromide, chloride, iodide, acetate and chromate salts.

The promoter which is used in accordance with the process of this invention may be any N-heterocyclic promoter which is at least partially soluble in the reaction mixture (e.g. has a solubility of at least about 10 ppm in the reaction mixture). Illustrative of typical N-heterocyclic compounds of this character include pyridine and its derivatives such as 3,5-lutidine, 2,6-methoxypyridine, 4-dimethylaminopyridine, the collidines and 2,6-lutidine. Also effective are polycyclic, N-heterocyclics such as quinoline, isoquinoline and substituted derivatives thereof such as 2,2-biquinoline, lepidine, and quinaldine. The preferred heterocyclic promoters contain two or more N-heterocyclic atoms per molecule, such as 2-ethylpyrazine, and include polycyclic N-heterocyclics such as 2,2'-dipyridyl, 2,3'-dipyridyl, 2,4'-dipyridyl, 2,2'-bipyrimidine, 2,2',2''-terpyridyl, 2,4,6-tris(2-pyridyl)-S-triazine, 4,4'-dipyridyl, 4,4'-dimethyl-2,2'-dipyridyl, pyrimidine, 2,2'-dipyridylamine, acridine, 1,10-phenantroline, 2,2'-bipyrazine, and 2,3-bis(2-pyridyl)pyrazine.

Generally, in the catalyst system the molar ratio of the ruthenium compound to the quaternary phosphonium salt will range from about 1:0.01 to about 1:100 or more and, preferably, will be from about 1:0.5 to about 1:20.

The quantity of ruthenium compound and the cobalt compound employed in the instant invention is not critical and may vary over a wide range. In general, the novel process is desirably conducted in the presence of a catalytically effective quantity of the active ruthenium species and of the cobalt species which gives the desired product in reasonable yield. The reaction proceeds when employing as little as about $1 \times 10^{-6}$ weight percent, and even lesser amounts of ruthenium together with about $1 \times 10^{-6}$ weight percent or less of cobalt, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 5 weight percent in conjunction with a cobalt concentration of from about $1 \times 10^{-5}$ to about 5 weight percent, based on the total weight of reaction mixture is generally desirable in the practice of this invention. The preferred ruthenium-to-cobalt atomic ratio is from 10:1 to 1:10.

The temperature range which can usefully be employed in these syntheses is a variable dependent upon other experimental factors, including the pressure, and the concentration and choice of the particular species of ruthenium catalyst among other things. The range of operability is from about 150° C. to 350° C. when superatmospheric pressure of syngas are employed. A narrow range of 180° C. to 250° C. represents the preferred temperature range.

Superatmospheric pressures of 30 atm or greater lead to substantial yields of alkanols by the process of this invention. A preferred operating range is from 130 atm to 600 atm, although pressures above 600 atm also provide useful yields of the desired alkanols.

The relative amounts of carbon monoxide and hydrogen which may be initially present in the syngas, i.e., synthesis gas, mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Esters of monocarboxylic acids may also be formed during the course of this desired alkanol synthesis. Most often these are ester derivatives of acetic acid such as methyl acetate, ethyl acetate and propyl acetate, which can be conveniently recovered from the reaction mixture. The advantage of this process is an improvement in the selectivity of alcohol relative to ester achieved by the use of the promoters of this invention. With, for example, the $Ru_3(CO)_{12}$—$Co_2(CO)_8$-2,2'-dipyridyl catalyst combination dispersed in $Bu_4PBr$, $C_1$-$C_4$ alkanols may comprise up to 66 wt % of the total liquid product (see Example II), with ethanol making up to 53 wt % of that fraction.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ethanol-rich product, and said material may be recovered by methods well known in the art, such as distillation, fractionation, extraction and the like. A fraction rich in the ruthenium and cobalt catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been in parts by weight; all temperatures are in degrees centigrade and all pressures in atmospheres (atm).

Various embodiments of the process of this invention are illustrated in the following examples which are to be considered not limitative.

EXAMPLE 1

A mixture of triruthenium dodecacarbonyl (4.0 mmole Ru, 0.852 g), dicobalt octacarbonyl (4.0 mmole Co, 0.684 g), and 2,2'-dipyridyl (4.0 mmole, 0.625 g) in tetrabutylphosphonium bromide (15.0 g, 44.2 mmole) is transferred in a glass liner under $N_2$ purge to an 850 ml capacity pressure reactor equipped with heating and means of agitation. The reactor is sealed, flushed with $CO/H_2$ and pressured to 136 atm with $CO/H_2$ (1:1). The mixture is heated to 230° C. with rocking, the pressure raised to 238 atm with $CO/H_2$ addition from a large surge tank and the reactor held at a temperature for 6 hours. Pressure is maintained at ca. 238 atm. by incremental additions of $CO/H_2$ from the surge tank.

On cooling, the reactor pressure (134 atm) is noted, a typical gas sample taken, and the excess gas removed. The deep-red liquid product (32.8 g) is analyzed by glc (weight percent) and Karl Fischer titration. Typical data are as follows:

| | |
|---|---|
| 31.3% ethanol | 9.9 methyl acetate |
| 22.5% methanol | 19.6% ethyl acetate |
| 4.6% propanols | 4.4% propyl acetates |
| 0.4% butanols | 1.1% water |

Here the liquid yield is: $32.8 - 17.2 = 15.6$ g.

The liquid yield increase is $[(32.8 - 17.2)/17.2] \times 100 = 91$ wt %.

The alkanol and acetate ester fractions are recovered from the crude liquid product by distillation. The dark brown liquid residue resolidifies upon cooling.

Analysis of the typical off-gas samples shows the presence of:

| | |
|---|---|
| 35% hydrogen | 16% carbon dioxide |
| 40% carbon monoxide | 5% methane |

It may be noted that:

$C_1$-$C_4$ alkanols comprise up to 59% of the total liquid products.

Ethanol makes up 31.3% of the total liquid product and 53% of the alkanol fraction.

EXAMPLE 2

Following the procedure of Example 1, the reactor is charged with a mixture of triruthenium dodecacarbonyl (4.0 mmole Ru, 0.852 g), dicobalt octacarbonyl (4.0 mmole Co., 0.684 g), 2,3-bis(2-pyridyl)pyrazine (4.0 mmole, 0.937 g) and tetrabutylphosphonium bromide (15.0 g).

After reaction, the 36.4 g of brown liquid product is recovered and analyzed. Typical data are as follows:

| | |
|---|---|
| 23.6% methanol | 8.2% methyl acetate |
| 34.5% ethanol | 14.8% ethyl acetate |
| 5.7% propanols | 3.7% propyl acetates |
| 0.1% butanols | 0.5% butyl acetates |

Here the liquid yield is: $36.4 - 17.5 = 18.9$ g.

It may be noted that:

The $C_1$-$C_4$ alkanols comprise 64% of the total liquid products. Ethanol makes up 34.5% of the total liquid product and 54% of the alkanol fraction.

EXAMPLE 3

Following the procedure of Example 1, the reactor is charged with a mixture of triruthenium dodecacarbonyl (4.0 mmole Ru, 0.852 g), dicobalt octacarbonyl (4.0 mmole Co, 0.684 g), 2,2'bipyrazine (0.380 g) and tetrabutylphosphonium bromide (15.0 g).

After reaction, the 37.3 g of brown liquid product is recovered and analyzed. Typical data are as follows:

| | |
|---|---|
| 19.4% methanol | 6.6% methyl acetate |

-continued

| 32.7% ethanol | 16.4% ethyl acetate |
| 8.6% propanols | 6.2% propyl acetates |
| 0.4% butanols | 1.3% butyl acetates |

Here the liquid yield is: 37.3−16.9=20.4 g.

It may be noted that:

The $C_1$-$C_4$ alkanols comprise 61% of the total liquid products. Ethanol makes up 32.7% of the total liquid product and 54% of the alkanol fraction.

EXAMPLE 4

Following the procedure of Example 1, the reactor is charged with a mixture of triruthenium dodecacarbonyl (4.0 mmole Ru, 0.852 g), dicobalt octacarbonyl (4.0 mmole Co, 0.684 g), 2-ethylpyrazine (4.0 mmole, 0.432 g) and tetrabutylphosphonium bromide (15.0 g).

After reaction, the 35.6 g of brown liquid product is recovered and analyzed. Typical data are as follows:

| 20.8% methanol | 7.2% methyl acetate |
| 33.3% ethanol | 16.0% ethyl acetate |
| 8.7% propanols | 6.1% propyl acetates |
| 0.5% butanols | 1.3% butyl acetates |

Here the liquid yield is: 35.6−17.0=18.6 g.

It may be noted that:

The $C_1$-$C_4$ alkanols comprise 63% of the crude liquid product. Ethanol makes up 33.3% of the total liquid product and 53% of the alkanol fraction.

COMPARATIVE EXAMPLE A

Following the procedures of Example 1, the reactor is charged with a mixture of triruthenium dodecacarbonyl (4.0 mmole Ru, 0.852 g), dicobalt octacarbonyl (4.0 mmole Co, 0.684 g) and tetrabutylphosphonium bromide (15.0 g). There is *no* N-heterocyclic promoter added in this comparative example.

After reaction, the 35.0 g of brown liquid product is recovered, and analyzed. Typical data are as follows:

| 13.0% methanol | 6.7% methyl acetate |
| 25.7% ethanol | 14.4% ethyl acetate |
| 10.1% propanols | 8.7% propyl acetates |
| 0.6% butanols | 2.0% butyl acetates |

Here the liquid yield is: 35.0−16.5=18.5 g.

However, it may be noted that in this comparative example, with no N-heterocyclic promoter:

The $C_1$-$C_4$ alkanols comprise only 49% of the total liquid products.

Ethanol makes up only 25.7% of the total liquid product.

EXAMPLES 5-15

In Examples 5-15, the data for which is recorded in Table I, the same procedure was used as in Example 1. However, different molar ratios of catalyst components were used and different types of N-heterocyclic promoters were used. Each synthesis was conducted under moderate operating pressures.

It may be noted that in Examples 5-11, using the $Ru_3(Co)_{12}$-$Co_2(CO)_8$-dipyridyl catalyst combination:

In Example 6, the $C_1$-$C_4$ alkanols comprise up to 64% of the total liquid oxygenates.

In Example 11, $C_1$-$C_4$ alkanol content reaches 66%.

Examples 12-15 illustrate the use of other N-heterocyclic promoters. Here is may be noted that:

In all four cases the $C_1$-$C_4$ alkanols comprise 58.7-61.5% of the total liquid oxygenates.

In all four examples the ethanol content is $\geq 28.0\%$.

TABLE 1

| Ex. | Catalyst Composition[a] | Melt | Liquid Product Composition (weight percent)[b,c] | | | |
| --- | --- | --- | --- | --- | --- | --- |
| | | | MeOH | EtOH | PrOH | BuOH |
| 5 | $Ru_3(CO)_{12}$—$Co_2(C0)_8$— ½ dipyridyl | $Bu_4PBr$ | 17.5 | 28.5 | 7.9 | 0.8 |
| 6 | $Ru_3(CO)_{12}$—$Co_2(CO)_8$— 2 dipyridyl | $Bu_4PBr$ | 40.3 | 21.5 | 1.7 | 0.9 |
| 7 | $Ru_3(CO)_{12}$—2[$Co_2(CO)_8$— dipyridyl] | $Bu_4PBr$ | 32.9 | 24.6 | 3.0 | 0.5 |
| 8 | $Ru_3(CO)_{12}$—¼[$Co_2(CO)_8$— dipyridyl] | $Bu_4PBr$ | 2.40 | 25.9 | 5.2 | 0.5 |
| 9 | $Ru_3(CO)_{12}$—¾[$Co_2(CO)_8$— dipyridyl] | $Bu_4PBr$ | 25.5 | 27.2 | 4.6 | 0.2 |
| 10 | $Ru_3(CO)_{12}$—$Co_2(CO)_8$— 2 dipyridyl[e] | $Bu_4PBr$ | 7.9 | 28.9 | 6.4 | |
| 11 | $Ru_3(CO)_{12}$—$Co_2(C0)_8$— dipyridyl[f] | $Bu_4PBr$ | 35.3 | 28.6 | 2.4 | |
| 12 | $Ru_3(CO)_{12}$—$Co_2(CO)_8$— 2,2'-bipyrimidine | $Bu_4PBr$ | 28.6 | 28.2 | 3.9 | 0.8 |
| 13 | $Ru_3(CO)_{12}$—$Co_2(CO)_8$— 2,3'-dipyridyl | $Bu_4PBr$ | 24.9 | 28.0 | 6.8 | 0.6 |
| 14 | $Ru_3(CO)_{12}$—$Co_2(CO)_8$— 2,4'-dipyridyl | $Bu_4PBr$ | 24.0 | 28.3 | 5.9 | 0.5 |
| 15 | $Ru_3(CO)_{12}$—$Co_2(CO)_8$ 2,4,6-tri(2-pyridyl)triazine | $Bu_4PBr$ | 28.2 | 29.4 | 2.1 | 0.3 |

TABLE I, PART 2

Table I, Part 2 shows the liquid product composition, including liquid yield, weight percent of acetate by-products and selectivity for $C_1$-$C_4$ alcohols.

TABLE I

| Ex. | Liquid Product Composition (wt %)[b,c] | | | | | Liquid[c] Yield (g) | $C_1$-$C_4$ Alcohol[d] Selectivity % |
| --- | --- | --- | --- | --- | --- | --- | --- |
| | MeOAc | EtOAc | PrOAc | BuOAc | $H_2O$ | | |
| 5 | 8.9 | 21.7 | 7.5 | 1.3 | 1.0 | 18.2 | 54.7 |

TABLE I-continued

| Ex. | Liquid Product Composition (wt %)[b,c] | | | | | Liquid[c] Yield (g) | C$_1$-C$_4$ Alcohol[d] Selectivity % |
|---|---|---|---|---|---|---|---|
| | MeOAc | EtOAc | PrOAc | BuOAc | H$_2$O | | |
| 6 | 13.2 | 8.6 | 0.7 | | 1.3 | 12.2 | 64.4 |
| 7 | 13.3 | 8.1 | 1.7 | 0.2 | 1.0 | 11.8 | 61.0 |
| 8 | 10.4 | 18.1 | 3.6 | 0.5 | 0.6 | 16.0 | 55.6 |
| 9 | 10.5 | 17.6 | 2.9 | 0.5 | 0.3 | 15.5 | 57.5 |
| 10 | 6.4 | 32.7 | 8.1 | 0.9 | 1.0 | 28.4 | 42.8 |
| 11 | 8.3 | 9.7 | 1.0 | 0.5 | | 12.0 | 66.3 |
| 12 | 12.1 | 15.0 | 2.6 | 0.4 | 0.7 | 15.4 | 61.5 |
| 13 | 9.6 | 15.7 | 4.4 | 0.8 | 1.0 | 19.1 | 60.3 |
| 14 | 9.4 | 16.4 | 4.2 | 0.7 | 1.1 | 18.8 | 58.7 |
| 15 | 17.2 | 14.2 | 1.3 | | 1.6 | 11.3 | 60.0 |

The following notations are applicable to Table I, both parts 1 and 2:
[a]Catalyst charge: Ru, 4.0 mmole; Co, 4.0 mmole; 2,2'-dipyridyl, 4.0 mmole; Bu$_4$PBr, 15.0 g
[b]Liquid product composition as determined by glc and Karl Fischer titration
[c]Run conditions: 230° C.; 238 atm; CO/H$_2$ (1:1); 6 hr.
[d](C$_1$-C$_4$ alcohols/liquid product) × 100
[e]Run for 18 hours
[f]Run with CO/H$_2$ 1:2

What is claimed is:

1. An improved process for making C$_1$-C$_4$ alkanols with an especially high proportion of ethanol which comprises contacting a mixture of synthesis gas (e.g. carbon monoxide and hydrogen) at a pressure of at least 30 atm and at a temperature of at least 150° C. with a catalyst system comprising a ruthenium-containing compound and a cobalt-containing compound dispersed in a low melting quaternary phosphonium salt wherein improved selectivity for total C$_1$-C$_4$ alkanols and ethanol in particular is achieved by use of an N-heterocyclic promoter.

2. The process of claim 1 wherein the process is conducted at a pressure of about 130 atm to about 600 atm.

3. The process of claim 1 wherein the process is conducted at a temperature of about 150° to about 350° C.

4. The process of claim 1 wherein the quaternary salt or base has a melting point less than about 180° C.

5. The process of claim 1 wherein the quaternary salt is a tetraalkylphosphonium salt.

6. The process of claim 5 wherein the alkyl groups contain 1-6 carbon atoms.

7. The process of claim 1 wherein the quaternary is a mixed alkylaryl phosphonium quaternary.

8. The process of claim 1 wherein the quaternary salt is tetrabutylphosphonium salt.

9. The process of claim 8 wherein the tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

10. The process of claim 1 wherein the ruthenium-containing compound is selected from the group consisting of one or more oxides of ruthenium, ruthenium salts of an organic carboxylic acid, ruthenium complexes with carbonyl-containing ligands and ruthenium carbonyl or hydrocarbonyl derivatives.

11. The process of claim 1 wherein the ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecarbonyl.

12. The process of claim 1 wherein said ruthenium-containing compound is triruthenium dodecacarbonyl.

13. The process of claim 1 wherein the cobalt-containing compound is selected from the group consisting of one or more oxides of cobalt, cobalt salts of an organic carboxylic acid, cobalt complexes with carbonyl-containing ligands, and cobalt carbonyl and hydrocarbonyl derivatives.

14. The process of claim 1 wherein the cobalt-containing compound is selected from the group consisting of dicobalt octacarbonyl, cobalt(III) acetylacetonate, cobalt(II) acetate, cobalt(II) propionate and cobalt(II) acetylacetonate.

15. The process of claim 15 wherein the cobalt-containing compound is dicobalt octacarbonyl.

16. The process of claim 1 wherein the N-heterocyclic promoter contains two or more N-heterocyclic atoms per molecule.

17. The process of claim 1 wherein the N-heterocyclic promoters are selected from the group consisting of 2,2'-dipyridyl, 2,2'-bipyrimidine, 2,3'-dipyridyl, 2,4'-dipyridyl, 2,3-bis(2-pyridyl)pyrazine, 2,2'-bipyrazine, 2-ethylpyrazine, and 2,4,6-tris(2-pyridyl)-S-triazine.

* * * * *